United States Patent
Malecki (10) Patent No.: US 7,193,577 B2
(45) Date of Patent: Mar. 20, 2007

(54) SYSTEM AND METHOD FOR REMOVING STREAMS OF DISTORTED HIGH-FREQUENCY ELECTROMAGNETIC RADIATION

(76) Inventor: Zbigniew Malecki, 108 Devonglen Drive, Kitchener (CA) N2E 2C5

( * ) Notice: Subject to any disclaimer, the term of this patent is extended or adjusted under 35 U.S.C. 154(b) by 21 days.

(21) Appl. No.: 11/065,154

(22) Filed: Feb. 25, 2005

(65) Prior Publication Data

US 2005/0200544 A1  Sep. 15, 2005

Related U.S. Application Data

(60) Provisional application No. 60/547,086, filed on Feb. 25, 2004.

(51) Int. Cl.
*H01Q 13/10* (2006.01)

(52) U.S. Cl. .................................................. 343/767

(58) Field of Classification Search ............. 343/767, 343/700 MS; 315/169
See application file for complete search history.

(56) References Cited

U.S. PATENT DOCUMENTS

| | | | |
|---|---|---|---|
| 2,853,624 A | 9/1958 | Wigner et al. | |
| 3,197,641 A | 7/1965 | Larkin | |
| 3,277,620 A | 10/1966 | Martin | |
| 3,608,280 A | 9/1971 | Martin | |
| 4,132,995 A | 1/1979 | Monser | |
| 4,801,807 A | 1/1989 | Jacobs | |
| 4,843,403 A | 6/1989 | Lalezari et al. | |
| 5,122,332 A | 6/1992 | Russell | |
| 5,153,378 A | 10/1992 | Garvy, Jr. | |
| 5,477,233 A | 12/1995 | Hemming et al. | |
| 5,519,408 A | 5/1996 | Schnetzer | |
| 5,590,031 A | 12/1996 | Mead, Jr. et al. | |
| 5,856,807 A | 1/1999 | Davis et al. | |
| 5,891,182 A | 4/1999 | Fleming | |
| 6,002,374 A | 12/1999 | Nicholas | |
| 6,249,006 B1 | 6/2001 | Sakiyama | |
| 6,320,548 B1 | 11/2001 | Harrell et al. | |
| 6,518,931 B1 | 2/2003 | Sievenpiper | |
| 6,839,036 B1 | 1/2005 | Apostolos et al. | |
| 6,844,851 B2 | 1/2005 | Yoon et al. | |
| 6,999,028 B2 * | 2/2006 | Egbert | 343/700 MS |
| 2001/0048400 A1 | 12/2001 | LaRochelle et al. | |
| 2002/0011189 A1 | 1/2002 | Leightner et al. | |
| 2002/0180655 A1 | 12/2002 | Mohuchy et al. | |
| 2003/0142026 A1 | 7/2003 | Hadden, IV et al. | |

(Continued)

FOREIGN PATENT DOCUMENTS

| | | |
|---|---|---|
| CA | 2139682 | 7/1996 |
| CA | 2161255 | 5/2000 |
| CA | 2374935 | 12/2000 |

OTHER PUBLICATIONS

Microwave Engineering—2nd Ed. (POZAR), 1998 (Chap. 8 & 12).
Antenna Theory Analysis and Design—2nd Ed. (BALANIS), 1997 (Chap. 1, 6, 8 & 10).
Introduction to Electric Circuits—3rd Ed. (Jackson), 1970 (Chap. 7 & 11).

(Continued)

*Primary Examiner*—Trinh Dinh
*Assistant Examiner*—Huedung Mancuso (57) ABSTRACT

A system for removing one or more streams of distorted high-frequency electromagnetic radiation. Each stream is directed substantially in a first direction from the Earth's surface and creates a distorted electromagnetic field. The system has an antenna for receiving the electromagnetic radiation and a capacitor electrically connected to the antenna. The capacitor converts the electromagnetic radiation into a form of potential energy with a frequency equivalent to zero and stores the potential energy. Each stream is substantially removed upon the conversion of the electromagnetic radiation into the potential energy.

14 Claims, 11 Drawing Sheets

U.S. PATENT DOCUMENTS

2004/0011972 A1   1/2004   Alishahi
2004/0041106 A1   3/2004   Masaki et al.
2005/0012672 A1   1/2005   Fisher
2005/0109879 A1*   5/2005   Patterson ............... 244/172
2005/0200544 A1*   9/2005   Malecki .................. 343/767
2005/0285541 A1*   12/2005   LeChevalier ........... 315/169.3

OTHER PUBLICATIONS

PCT/CA2005/000283, Feb. 25, 2005 Int'l Search Report.
The California EMF Program—Final Report, Jun. 2002 (pp. 400)—See attached Sheet for Pertinent Pages.
PCT/CA2005/000283, Malecki, Int'l Preliminary Report on Patentability.

* cited by examiner

SYSTEM AND METHOD FOR REMOVING STREAMS OF DISTORTED HIGH-FREQUENCY ELECTROMAGNETIC RADIATION

This application claims the benefit of U.S. Provisional Application No. 60/547,086, filed Feb. 25, 2004.

FIELD OF THE INVENTION

This invention is related to a system for removing streams of distorted high-frequency electromagnetic radiation.

BACKGROUND OF THE INVENTION

Electromagnetic waves are generally thought to have an adverse effect on the health of human beings, or at least the potential to cause such an adverse effect. Electromagnetic waves emanating from electric power transmission lines or transformers have been found to adversely affect the health of human beings, although the mechanism whereby electromagnetic waves adversely affect the human body is not well understood.

Figure 1A:
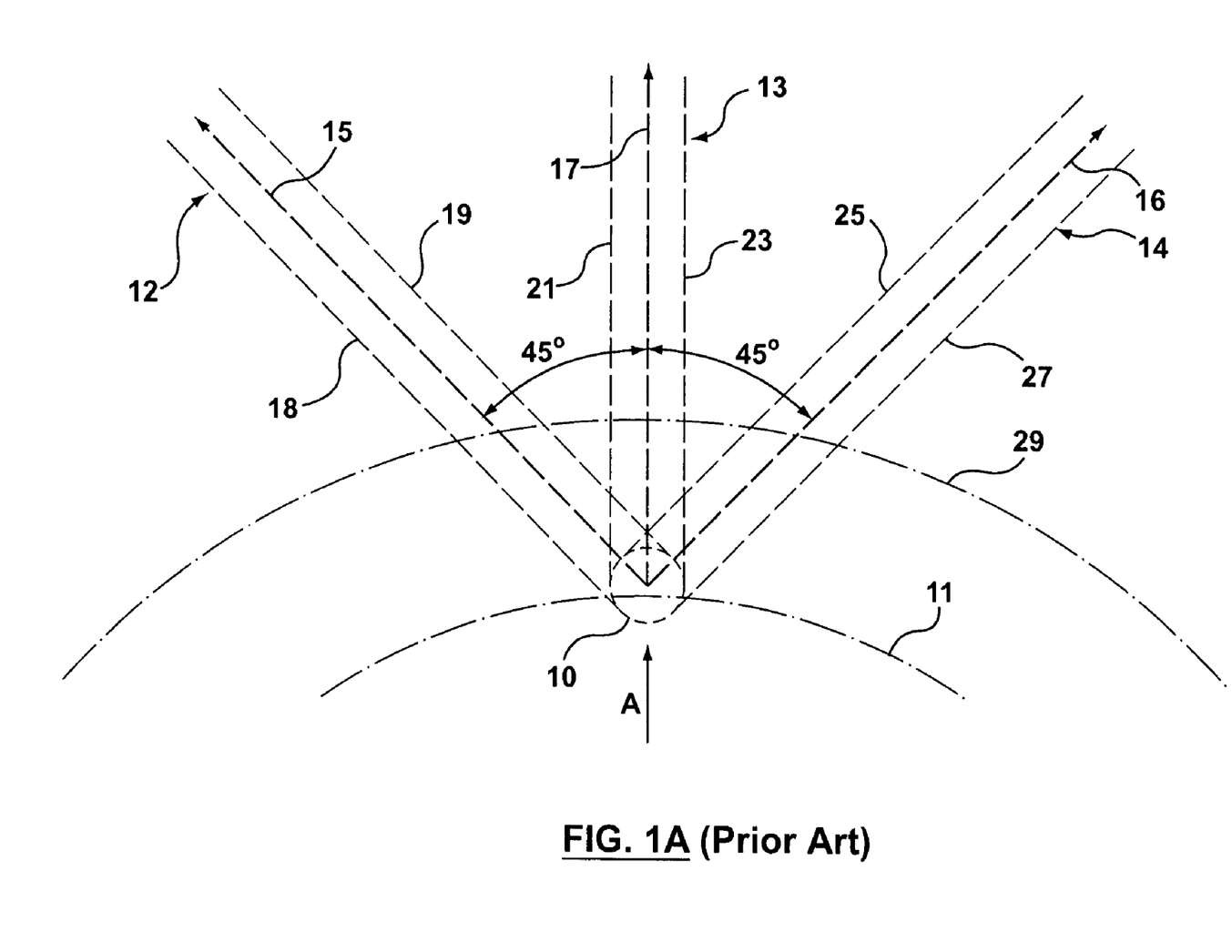
FIG. 1A (previously described) is a schematic diagram showing streams of distorted high-frequency electromagnetic radiation.
Figure 1B:
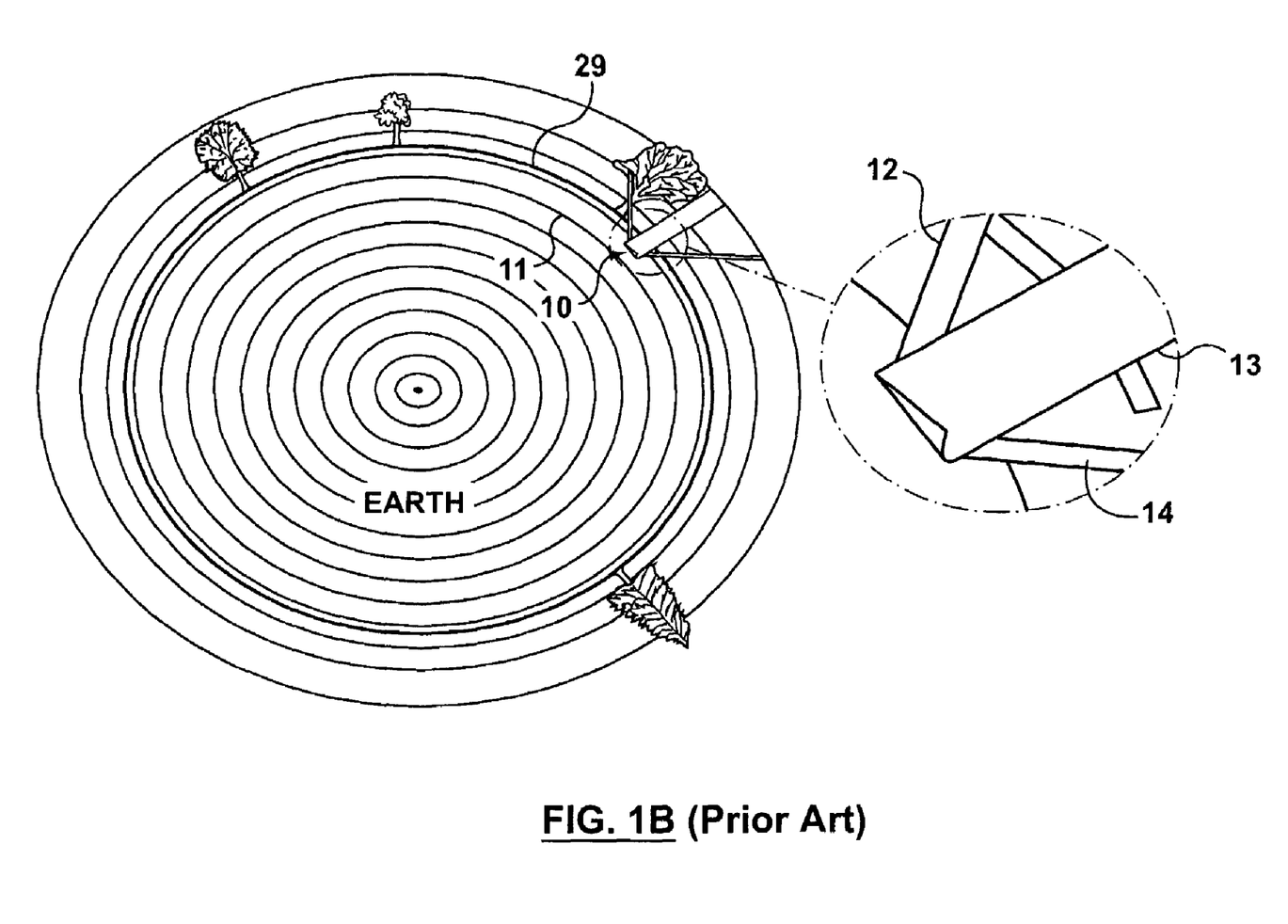
FIG. 1B (also previously described) is a schematic diagram showing a possible mechanism for the generation of electromagnetic radiation and the creation of streams of distorted high-frequency electromagnetic radiation, drawn at a smaller scale.

Very high-frequency electromagnetic waves have been shown to emanate from the Earth. The original source, or cause, of these electromagnetic waves has not been identified. However, this electromagnetic radiation does appear to result from natural causes. It appears that these high-frequency electromagnetic waves typically are directed in a direction which is substantially orthogonal to the Earth's surface, if there is nothing present in the Earth's crust to disturb the electromagnetic waves. However, these electromagnetic waves appear to be affected by different materials (e.g., underground running water, or cavities, or certain types of mineral deposits), which can distort or disturb the electromagnetic waves (as shown in FIGS. 1A and 1B). These disturbed and/or distorted parts of the electromagnetic waves (collectively hereinafter referred to as "streams of distorted high-frequency electromagnetic radiation") are of particular concern because they appear to have an adverse effect upon the human body, as will be described.

The streams of distorted high-frequency electromagnetic radiation are parts of very high-frequency electromagnetic waves (e.g., approximately 150 GHz or greater), and they appear to be relatively widespread. Typical structures (e.g., houses, or office buildings) are substantially transparent to these electromagnetic waves. This is in contrast to, for example, the shielding effect a structure can exhibit relative to a low-frequency electromagnetic wave.

The streams of distorted high-frequency electromagnetic radiation also appear generally to be characterized by generally small wavelengths (e.g., microwaves or nanowaves). However, as these streams of distorted electromagnetic radiation can also be modulated by longer-wavelength electromagnetic waves, it is possible that these streams can be characterized by somewhat longer wavelengths in these circumstances.

As is well known, the Earth has a magnetic field operational between the north pole and the south pole. However, as the lines of magnetic force are virtually parallel to the Earth's surface, these streams of high-frequency electromagnetic waves do not appear to be directly related to the Earth's magnetic field.

FIG. 1A shows an underground anomaly 10 which disturbs the electromagnetic waves 11 to produce streams of distorted high-frequency electromagnetic radiation 12, 13, and 14. The strength, or intensity, of each of the streams 12, 14 generally appears to be approximately one-third of the intensity of the stream 13. Also, each of the streams 12, 14 has a path 15, 16 respectively deviating from a path 17 of the stream 13 by approximately 45°.

As can be seen in FIG. 1A, the electromagnetic waves 11 apparently move generally outwardly from the Earth's center, in the direction indicated by arrow "A". The streams 12, 13, and 14 have well-defined edges, or sides, which appear to be related to the extent of the anomaly 10. For example, as shown in FIG. 1A, the stream 12 has sides 18, 19; the stream 13 has sides 21, 23; and the stream 14 has sides 25, 27. The path 17 of the stream 13 is substantially orthogonal to the Earth's surface 29. A schematic diagram showing the manner in which the electromagnetic waves 11 are thought to emanate in a direction radially outward from the Earth's center until disturbed is provided in FIG. 1B.

Figure 1C:
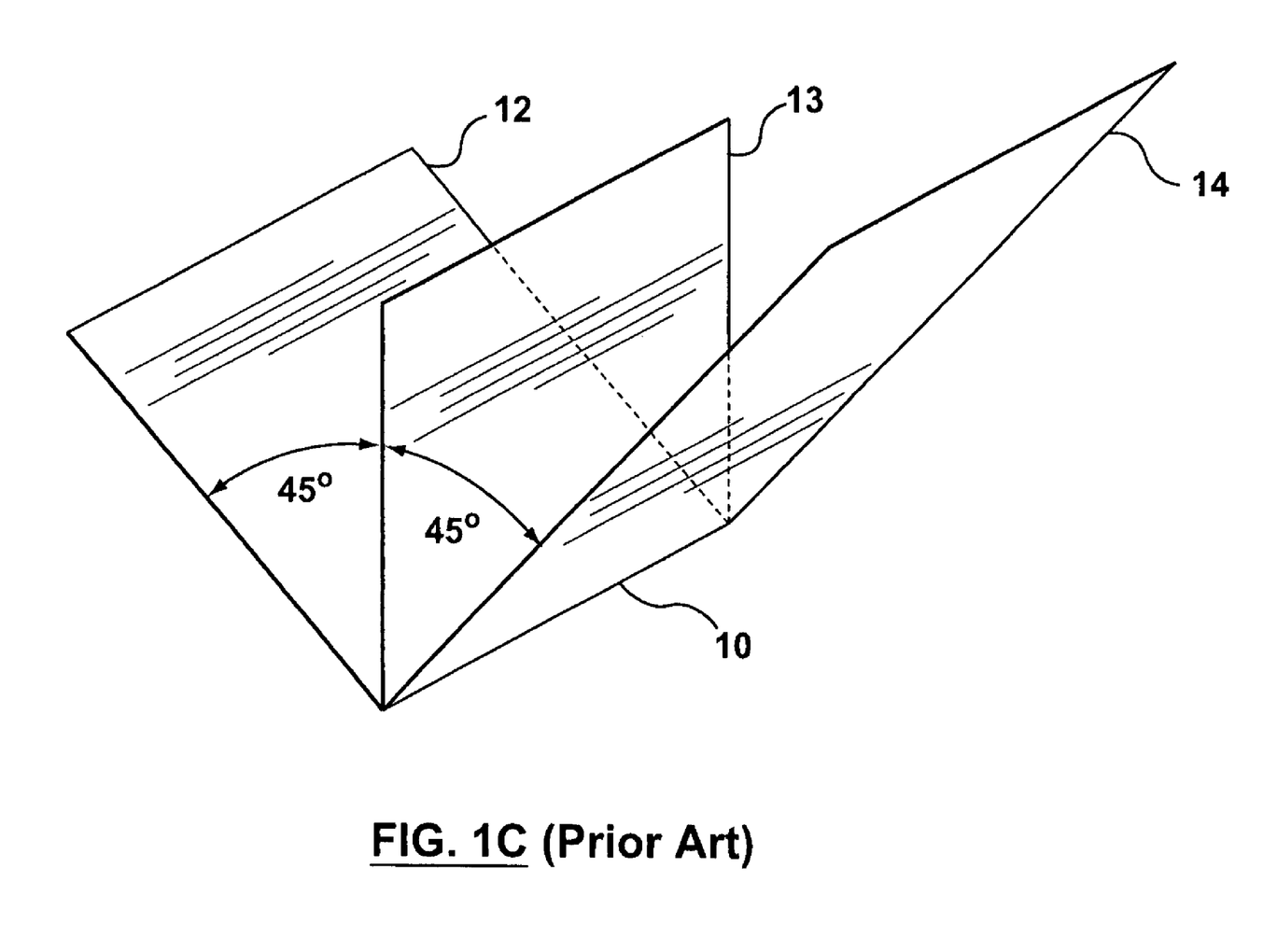
FIG. 1C (also previously described) is a schematic diagram of streams of distorted high-frequency electromagnetic radiation caused by an anomaly, drawn at a larger scale.
Figure 1D:
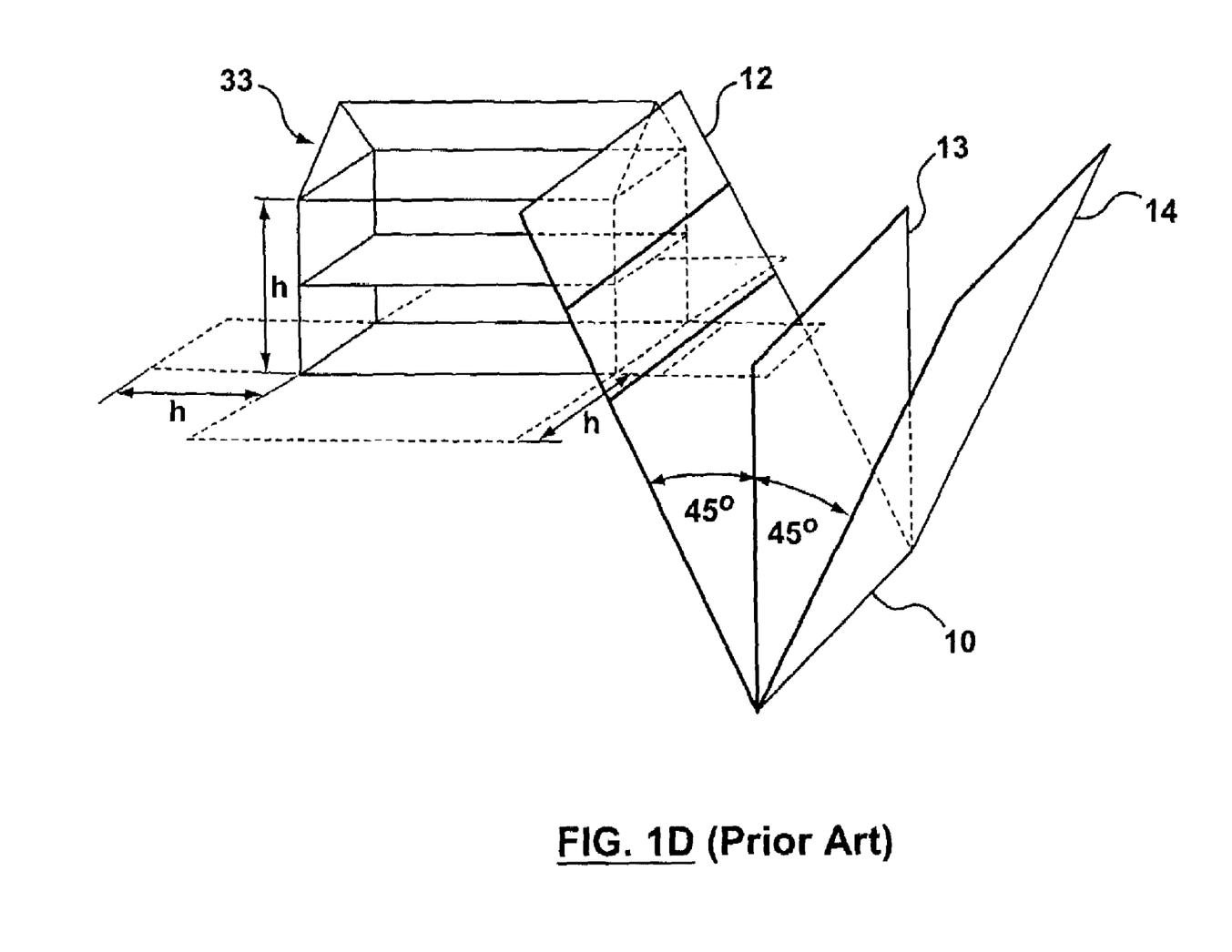
FIG. 1D (also previously described) is a schematic diagram of streams of distorted high-frequency electromagnetic radiation positioned near a structure.

FIG. 1C provides an isometric view in which the streams 12, 13, and 14 are shown. In FIG. 1D, the significance of the directions of the streams 12, 13, and 14 can be seen. A structure 33 is shown in FIG. 1D which is located substantially on or at the Earth's surface 29. In this example, the stream 12 is shown to pass through the structure 33 at different levels.

As can be seen in FIGS. 1C and 1D, the streams 12, 13 and 14 are three-dimensional regions which are downstream (i.e., relative to the electromagnetic radiation 11) from the anomaly 10. In these streams 12, 13, and 14, the electromagnetic radiation 11 appears to be distorted, relative to the electromagnetic radiation 11 upstream from the anomaly 10. Accordingly, electromagnetic fields which are also distorted are created by these streams of distorted electromagnetic radiation. The distortions apparently are caused by the anomaly 10.

Figure 1E:
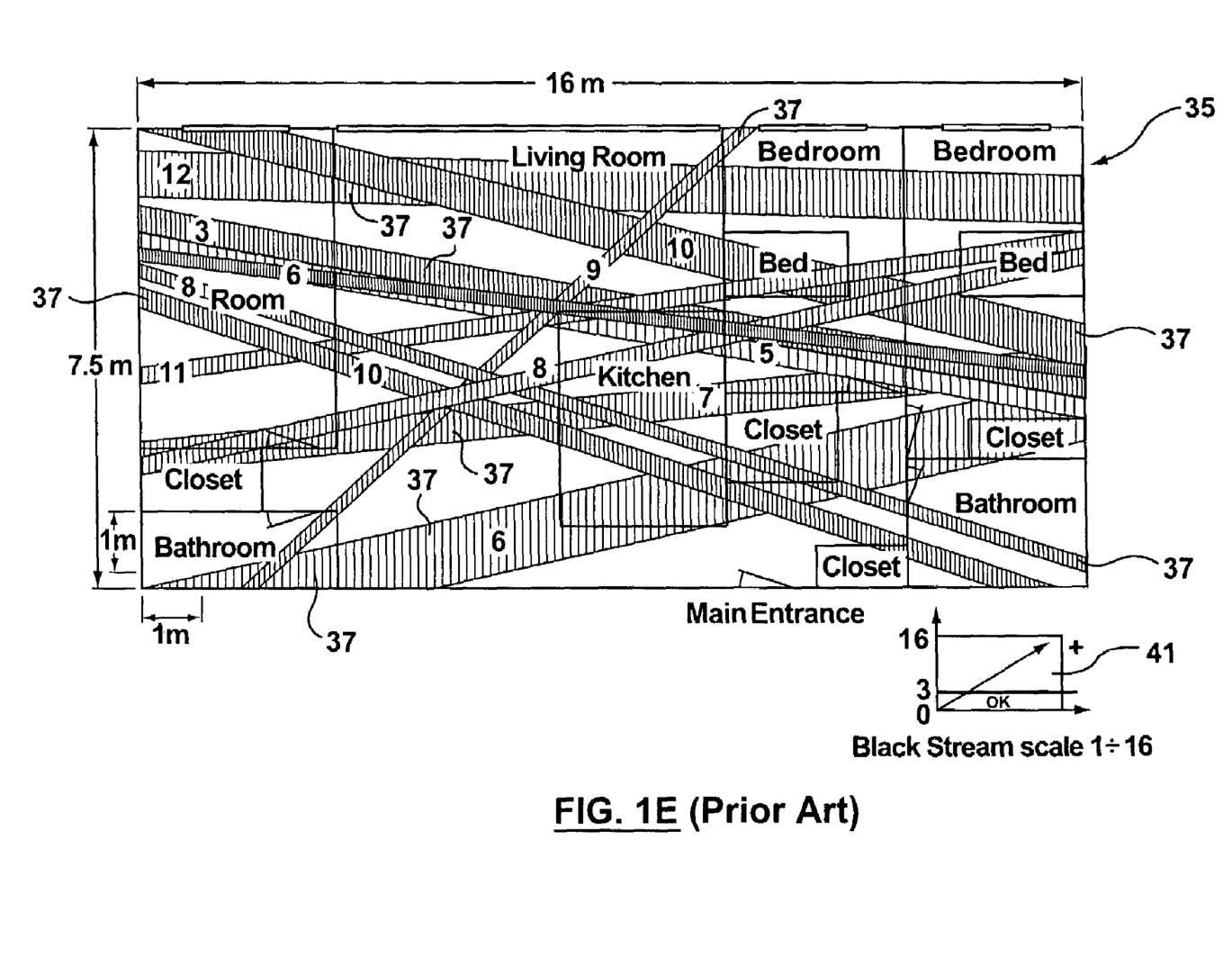
FIG. 1E (also previously described) is a plan view of a house showing electromagnetic fields resulting from streams of distorted high-frequency electromagnetic radiation.

It will also be understood that, for illustration, only one anomaly 10 has been shown. However, in many cases, there are a number of streams passing through the structure. For example, FIG. 1E shows a house plan (for one level of a house 35) in which a large number of streams of distorted high-frequency electromagnetic radiation 37 are present. FIG. 1E shows the intersection of the streams 37 with the floor of the house 35. (For clarity of illustration, element numbers for only a few of the streams 37 are provided in FIG. 1E. The numbers in circles in FIG. 1E represent different intensities based on a scale 41 provided in FIG. 1E.) It is thought that, where several streams of distorted electromagnetic fields are present, they are due to a number of anomalies in the Earth's crust in the vicinity of the house. Typically, the streams appear to have different intensities, for example, as indicated by the numbers in circles in FIG. 1E.

In summary, and as can be seen in FIG. 1E, the streams of distorted electromagnetic radiation appear to be very sharply-defined, in contrast to the typically somewhat ill-defined boundaries of electromagnetic fields generally. Also, each stream appears to have a path in a clearly-defined direction. This indicates that the streams are the result of a distorting, or disturbing, obstacle (i.e., an anomaly) which acts to distort the electromagnetic radiation in a fashion similar to a stone in a stream, to create a downstream zone shadowing the obstacle, in which the wave patterns are disturbed. However, it will be understood that the foregoing is only a plausible description of natural phenomena in respect of which more research is required.

In "An Evaluation of the Possible Risks from Electric and Magnetic Fields (EMFs) from Power Lines, Internal Wiring, Electrical Occupations, and Appliances" (Final Report, June 2002), the California EMF Program (California Electric Magnetic Fields Program, a project of the California Department of Health Services and the Public Health Institute) concluded:
1. that man-made electromagnetic fields can be harmful to the human body; and
2. that exposures of 2–16 milligauss are substantially equally harmful.

The Final Report is available at:
www.dhs.ca.gov/ps/deode/ehib/emf/RiskEvaluation/riskeval.html.

Figure 1F:
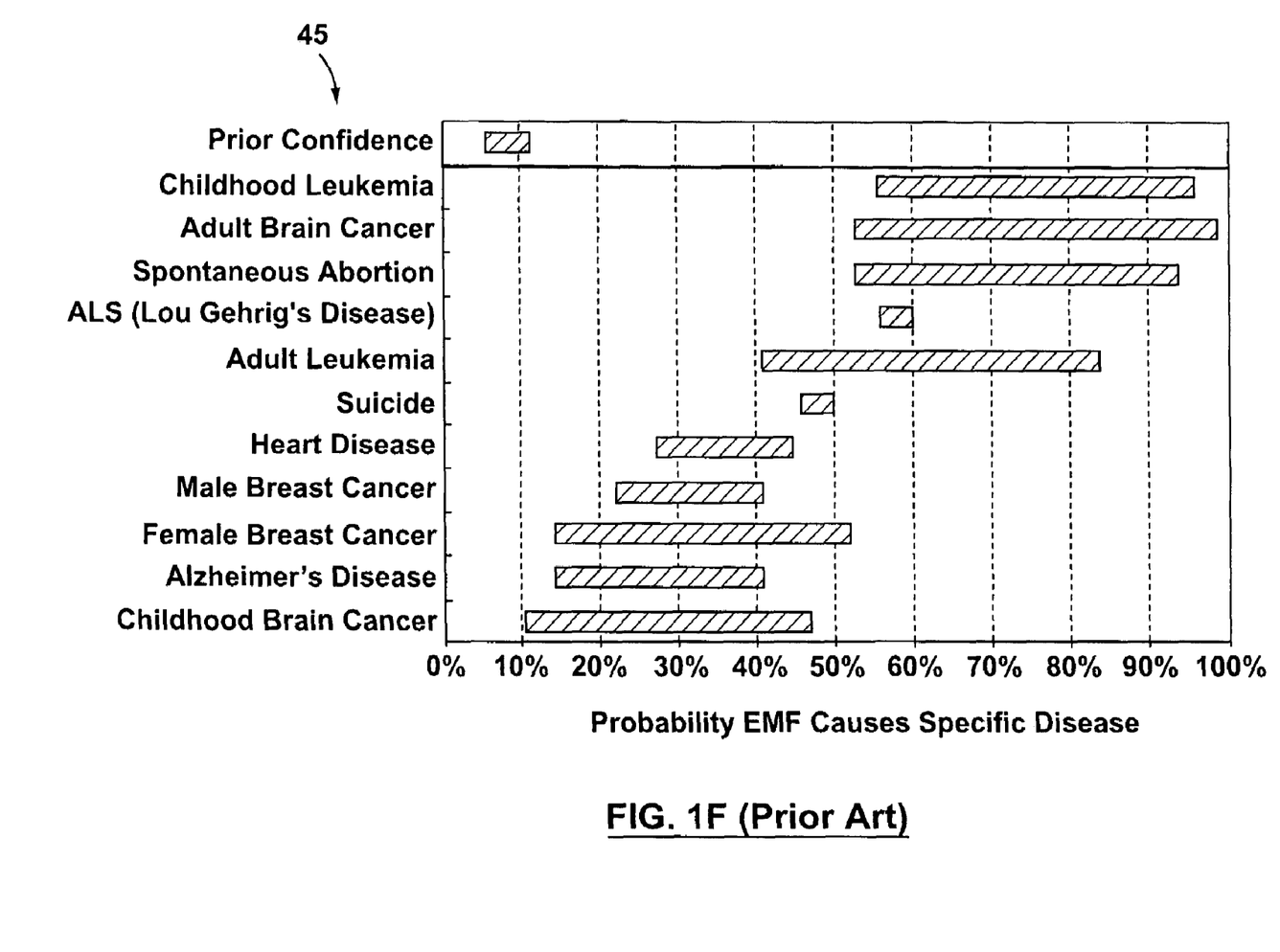
FIG. 1F (also previously described) is a graph showing estimated probabilities that man-made electromagnetic fields cause certain diseases.

FIG. 1F is a graph 45 showing the California EMF Program's conclusions regarding the probabilities of certain illnesses occurring due to man-made electromagnetic radiation.

As noted above, a mechanistic explanation of the effects of the streams of distorted high-frequency electromagnetic waves has not been developed. One possible explanation for the apparently harmful effects of man-made electromagnetic radiation is that the human body's immune system is activated to resist such radiation because it is inconsistent with the electromagnetic radiation which the immune system recognizes as normal.

Similarly, it is possible that the distortion of the electromagnetic radiation apparently caused by anomalies in the Earth is, like man-made electromagnetic radiation, identified by the immune system as foreign. According to this theory, the human body's immune system reacts to the distortions in the electromagnetic radiation by activating itself, i.e., the immune system recognizes distorted high-frequency electromagnetic radiation as anomalous, i.e., a "foreign" influence inside the body, and therefore is activated to defend against this potentially harmful "intruder".

If the foregoing is accurate, then the distortions in the streams of distorted electromagnetic radiation have an effect on the immune system which is very much like the effect of man-made electromagnetic fields. The distortions of high-frequency electromagnetic radiation result in stress on the immune system because the distortions differ from the typical, natural electromagnetic radiation which, due to evolution over many years, does not cause activation of the immune system. According to this theory, it is the distortions of the electromagnetic radiation, rather than the electromagnetic radiation itself, which is harmful, or potentially harmful.

Activation of the immune system appears to be substantially constant while a subject is in a distorted high-frequency electromagnetic field, and frequent and repeated exposure apparently tends to have a cumulative effect. Ultimately, this stress can result in the immune system becoming less able to respond to other threats, such as infections or other foreign agents which cause illness. Because of the weakening of the immune system, the subject's body is more seriously affected by illnesses which it might otherwise be able to resist.

There is therefore a need for a device which overcomes or mitigates one or more of the disadvantages of the prior art.

SUMMARY OF THE INVENTION

In its broad aspects, the invention provides a system for removing one or more streams of distorted high-frequency electromagnetic radiation. Each stream is directed substantially in a first direction from the Earth's surface and creates a distorted electromagnetic field. The system has an antenna for receiving the electromagnetic radiation and a capacitor electrically connected to the antenna. The capacitor converts the electromagnetic radiation into a form of potential energy with a frequency equivalent to zero and stores the potential energy. The result is that each stream is substantially removed upon the conversion of the electromagnetic radiation into the potential energy.

In another aspect, the invention additionally includes a conductor element for conducting a current flow from the capacitor to a grounding body. The capacitor includes a terminal having a first electrical potential (created by the potential energy) at the terminal. The conductor element is electrically connected to the capacitor at the terminal. Also, the grounding body has a second electrical potential lower than the first electrical potential, to create a difference of potentials. The current flow is caused by the difference of potentials between the capacitor and the grounding body.

In yet another aspect, the capacitor and the antenna are included in an interior assembly. The interior assembly is substantially contained in a housing including one insulating material.

In another of its aspects, the housing includes an inner shell made of a first insulating material and an outer shell made of a second insulating material.

In yet another aspect, the interior assembly includes one or more antenna elements and one or more support structures to position each antenna element so that each antenna element is aligned substantially in a second direction which is substantially orthogonal to the first direction.

In another of its aspects, each antenna element includes a disk of relatively electrically conductive material having a predetermined thickness measured substantially in the first direction and a predetermined radius measured substantially in the second direction to an outer edge with one or more notches therein. The notch includes an opening extending inwardly from the outer edge through the disk substantially parallel to the first direction.

In yet another aspect, each antenna element includes a top surface which is substantially planar and a substantially planar bottom surface disposed substantially parallel to the top surface, said surfaces being positioned substantially orthogonal to the first direction.

In another aspect, each antenna element includes one or more bent portions disposed adjacent to the notch and a remainder portion positioned adjacent to each bent portion. Each bent portion has a top surface and a substantially opposed bottom surface, and each of the top and bottom surfaces are non-coplanar with a top surface and a bottom surface of the remainder portion respectively. Also, each of the top and bottom surfaces of the remainder portion are substantially planar and substantially parallel to each other. The top and bottom surfaces of the remainder portion are positioned substantially orthogonally to the first direction.

In yet another aspect, the interior assembly comprises a plurality of antenna elements.

In another of its aspects, each antenna element has a preselected shape selected to provide coverage with respect to the streams of distorted high-frequency electromagnetic radiation over a predetermined geographic area.

In another aspect, the interior assembly includes two or more antenna elements, each antenna element having a preselected shape selected to provide coverage over two or more corresponding predetermined areas.

In yet another aspect, the predetermined thickness of each antenna element is selected to provide coverage over a preselected distance from each antenna element.

In another of its aspects, the invention provides a system for removing one or more streams of distorted high-frequency electromagnetic radiation. Each stream is directed substantially in a first direction from the Earth's surface and creates a distorted electromagnetic field. The system has two or more antennas for receiving the electromagnetic radiation, one or more capacitors electrically connected to the antennas, and a conductor assembly. The capacitor converts the electromagnetic radiation into a form of potential energy with a frequency equivalent to zero, and stores the potential energy to create a first electrical potential at a terminal of the capacitor. The conductor assembly is for conducting a current flow from the capacitor to a grounding body. The grounding body has a second electrical potential lower than the first electrical potential to create a difference of potentials. The conductor assembly includes a first conductor portion electrically connecting the antenna and the terminal on the capacitor, and a second conductor portion electrically connected to the terminal for conducting the current flow from the capacitor to the grounding body. The current flow is caused by the differences of potentials. The result is that the stream is substantially removed upon the conversion of the electromagnetic radiation into the potential energy.

BRIEF DESCRIPTION OF THE DRAWINGS

The invention will be better understood with reference to the drawings, in which.

DETAILED DESCRIPTION OF THE INVENTION

Figure 2A:
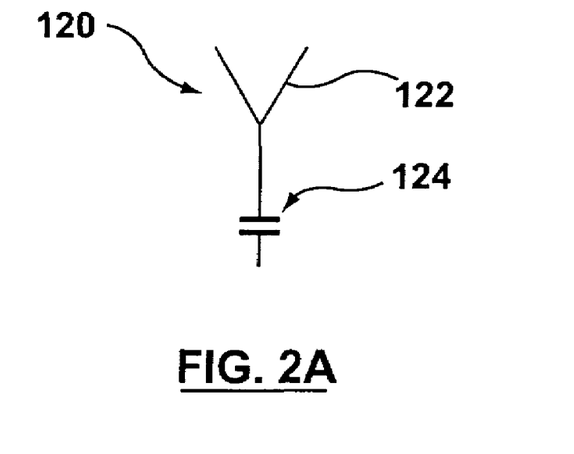
FIG. 2A is a schematic (circuit) diagram of a preferred embodiment of the system of the invention.

Reference is first made to FIG. 2A to describe an embodiment of a system in accordance with the invention indicated generally by the numeral 120. The system 120 is for removing one or more streams of distorted high-frequency electromagnetic radiation which are directed substantially in a first direction from the Earth's surface and create a distorted electromagnetic field. As shown in FIG. 2A, the system 120 includes an antenna 122 for receiving the electromagnetic radiation, and a capacitor 124. The capacitor 124, which is electrically connected to the antenna 122, converts the electromagnetic radiation into a form of potential energy with a frequency equivalent to zero and stores the potential energy. The result is that the distortions are substantially removed from the electromagnetic field upon the conversion of the electromagnetic radiation into potential energy.

Additional embodiments of the invention are shown in FIGS. 2B, 2C, and 3–9. In FIGS. 2B, 2C, and 3–9, elements are numbered so as to correspond to like elements shown in FIG. 2A.

Figure 2B:
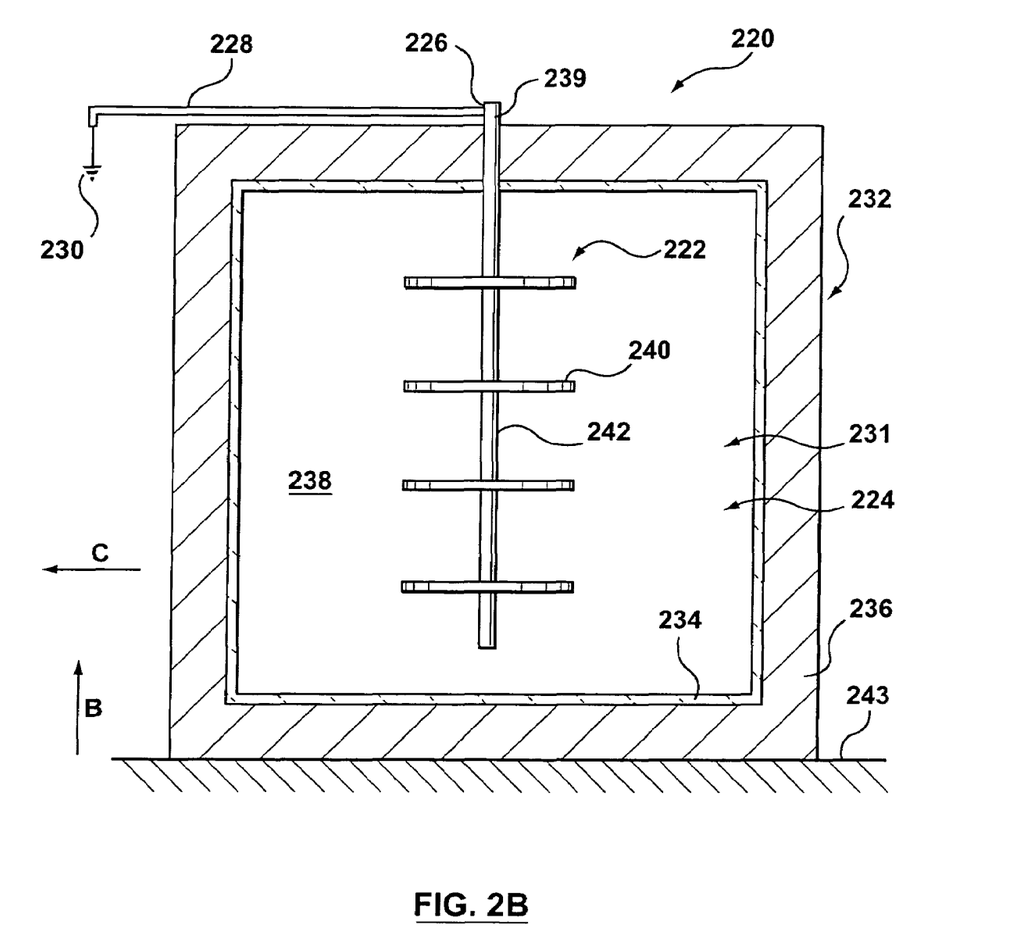
FIG. 2B is a cross-section of an alternative embodiment of the system of the invention, drawn at a larger scale.
Figure 2C:
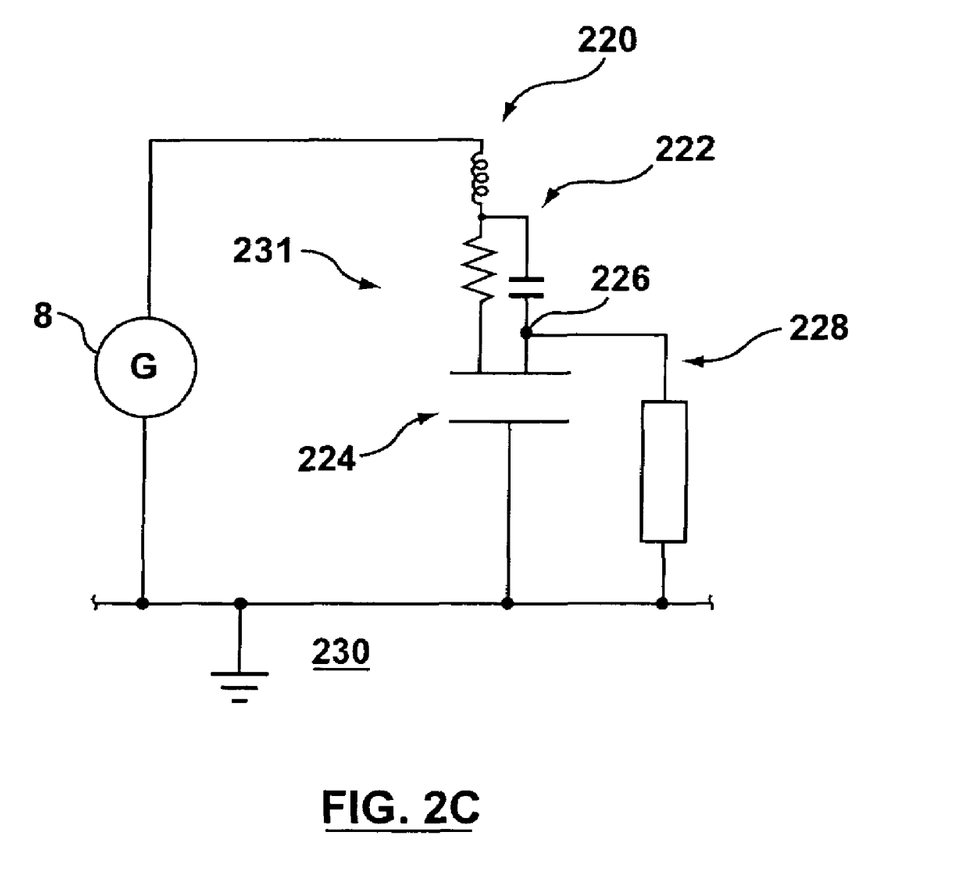
FIG. 2C is a schematic (circuit) diagram of the system of FIG. 2B.
Figure 3:
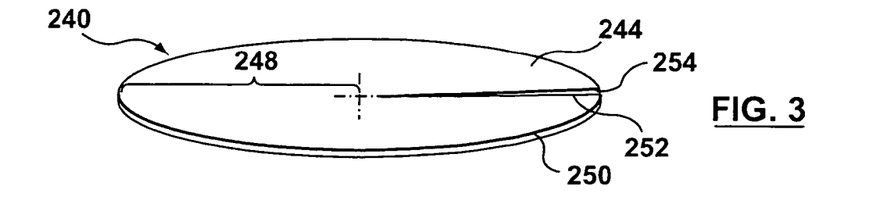
FIG. 3 is an isometric view of a preferred embodiment of an antenna element of the invention, drawn at a larger scale.
Figure 5:
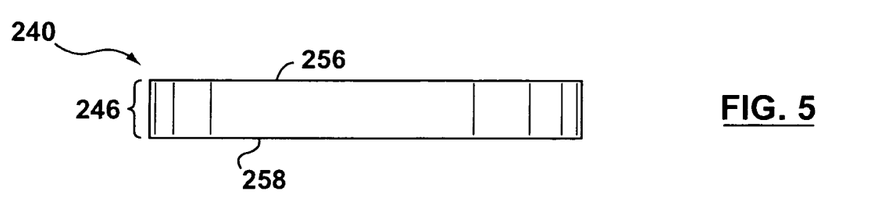
FIG. 5 is a side view of the antenna element of FIG. 3, drawn at a smaller scale.

A preferred embodiment of a system in accordance with the invention is indicated generally by the numeral 220 and is shown in FIGS. 2B, 3, and 5. The system 220 includes an antenna 222 and a capacitor 224. As can be seen in FIGS. 2B and 2C, the capacitor 224 preferably has a terminal 220. In the preferred embodiment, and as shown in FIGS. 2B and 2C, the system 220 also includes a conductor element 228 for conducting a current flow from the capacitor 224 to a grounding body 230. As will be described, the grounding body 230 could be the Earth or any other suitable body. Preferably, the conductor element 228 is electrically connected to the capacitor 224 at the terminal 226. The capacitor 224 has a first electrical potential created by the potential energy at the terminal 226. Because the grounding body 230 has a second electrical potential which is lower than the first electrical potential, a difference of potentials (or potential difference) is thereby created. The current flow from the capacitor 224 to the grounding body 230 is caused by the difference of potentials.

An unidentified source 8 is included in the circuit diagram of FIG. 2C.

Preferably, and as shown in FIG. 2B, the capacitor 224 and the antenna 222 are included together in an interior assembly 231 which is substantially contained in a housing 232 comprising one or more insulating materials. The housing 232 preferably includes an inner shell 234, and an outer shell 236 which substantially encompasses and supports the inner shell 234. It is preferred that the inner shell 234 is made of glass and the outer shell 236 is made of concrete, but any suitable materials could be used.

As is known in the art, the capacitor 224 includes a dielectric element 238. Preferably, the dielectric element 238 is a liquid dielectric, but any suitable dielectric could be used. Also, the antenna 222 could be a dipole antenna, or any suitable type of antenna.

In the preferred embodiment, an exposed portion 239 of the interior assembly 231 extends outside the housing 232 (FIG. 2B). The terminal 226 is positioned on the exposed portion 239, and location is advantageous because the conducting element 228 is disposed entirely outside the housing 232, and insulated from the dielectric element 238.

A particular stream of high-frequency electromagnetic waves has a path in a first direction, and for the purposes of illustration in FIG. 2B, the first direction is generally as indicated by arrow "B". It will be understood, however, that the system 220 is typically used to remove a plurality of streams of distorted electromagnetic radiation, each of which may have a path with a different direction. However, as described above, the more intense streams generally follow a path which is substantially orthogonal to the Earth's surface. Preferably, the interior assembly 231 includes one or more antenna elements 240 and a support structure 242 to position the antenna elements 240 so that the antenna elements 240 are aligned substantially in a second direction which is substantially orthogonal to the first direction. In FIG. 2B, the second direction is indicated by the arrow "C".

In use, the antenna elements 240 are preferably positioned in the housing 232 so that, when the housing 232 is set upon a floor surface 243 (FIG. 2B), the antenna element 240 is aligned substantially in the second direction. This maximizes the efficiency of the antenna element 240 in receiving the streams of high-frequency electromagnetic radiation. The capacitor 224 converts the received electromagnetic radiation into potential energy, and stores the potential energy. Once the capacity of the capacitor 224 to hold the potential energy is exceeded, the potential energy is to be discharged. The discharge occurs by virtue of the flow of current through the conductor element 228 from the capacitor 224 (at the terminal 226) to the grounding body 230.

It will be understood that, in the system 120, the potential energy accumulates (i.e., is stored) in the capacitor 124. Once the capacity of the capacitor 124 has been reached, the system 120 would no longer be effective to remove the distortions from the streams of electromagnetic radiation. From time to time, therefore, discharge of the system 120 is required, to enable the system 120 to continue functioning.

In order to protect those within a structure (e.g., a house or any other type of building), the system 220 is positioned within the structure, and the conductor element 228 is connected to any appropriate grounding body 230, as is known in the art. As will be described, it is preferable that the antenna 222 be appropriately sized and configured to provide coverage for the entire structure. Preferably, the system 220 is positioned in the lowest part (e.g., the basement) of the structure, for example, with the conductor element connected to a metal plumbing pipe to provide the grounding body.

It will also be understood that the system 220 could be used to provide protection for the occupants of a vehicle (not shown). In this situation, the system 220 is preferably a relatively small unit, and the conductor element 228 is preferably connected to a metal body and/or frame of the vehicle, so that the body and/or frame is used as the grounding body 230. Also, the system 220 is preferably located in the lowest part of the vehicle body.

In addition, a relatively small version of the system 120 could be carried on one's person. In that case, discharge could be effected by the wearer of the unit on a regular basis, in order to avoid a relatively high potential being stored in the capacitor 124.

As can be seen in FIGS. 2B, 3, and 5, the antenna element 240 is preferably a disk 244 of electrically conductive material which has a predetermined thickness 246 measured substantially in the first direction, and a predetermined radius 248 measured substantially in the second direction to an outer edge 250. Preferably, the disk 244 has one or more notches 252 therein. Each notch includes an opening 254 (FIG. 3) extending inwardly from the outer edge through the disk 244 substantially parallel to the first direction.

As can be seen in FIGS. 3 and 5, antenna element 240 preferably also includes a top surface 256 and an opposed bottom surface 258. Both the top surface 256 and the bottom surface 258 are substantially planar, and they are also preferably positioned substantially parallel to each other. The surfaces 256, 258 are preferably positioned substantially orthogonal to the first direction.

The thickness 246 of the antenna element 240 has a direct impact on the range of the antenna 222. The greater the thickness, the greater the range. In addition, where more than one antenna element is used, the range of the antenna including the antenna elements varies based on the total thicknesses of the antenna elements. For example, a copper disk with a thickness of approximately 0.016 cm. has a range of about 22 meters. Another copper disk with a thickness of 0.008 cm. has a range of approximately 12.5 meters. Because of the circular shape of the disks, the coverage provided by them is substantially circular.

Also, the range of an antenna varies in a direct relationship to the areas of the top surface and the bottom surface of the antenna elements.

Figure 4:
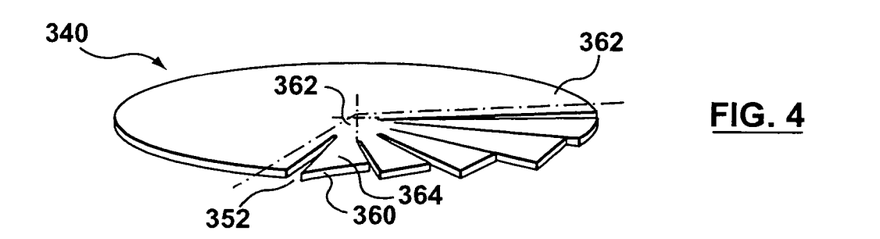
FIG. 4 is an isometric view of an alternative embodiment of the antenna element.
Figure 6:
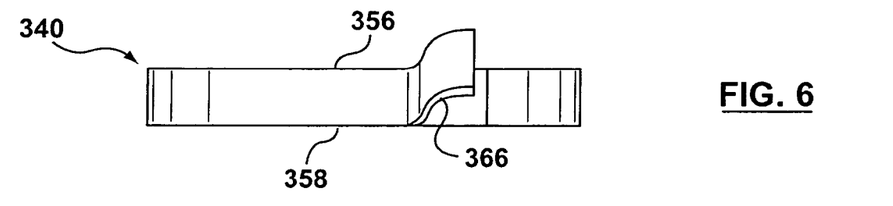
FIG. 6 is a side view of the antenna element of FIG. 4.

An alternative embodiment of a system includes an antenna element 340 (FIGS. 4 and 6). The antenna element 340 includes one or more bent portions 360 in a disk 344. The bent portion 360 is positioned adjacent to one or more notches 352. In addition, the disk 344 includes a remainder portion 362 positioned adjacent to the bent portion 360. The bent portion 360 has a top surface 364 and a substantially opposed bottom surface 366. Each of the top and bottom surfaces 364, 366 is non-coplanar with a top surface 356 and a bottom surface 358 of the remainder portion 362 respectively. Preferably, each of the top and bottom surfaces 356, 358 of the remainder portion 362 is substantially planar and they are substantially parallel to each other. Also, it is preferred that the top and bottom surfaces 356, 358 of the remainder portion 362 are positioned substantially orthogonally to the first direction.

It will be understood that what has been described is a preferred embodiment, and other arrangements are feasible. For example, the top and bottom surfaces 356, 358 of the remainder portion 362 need not necessarily be planar, and they need not necessarily be parallel to each other.

An additional effect is provided by the system including the antenna elements 340, apparently due to the bent portions 360. A human being (not shown) positioned anywhere in a geographic area protected by the system 320 is subjected to a massaging effect over the entire body. The massaging effect has been found to be beneficial to those suffering from various ailments, including chronic pain. In the preferred embodiment, the greatest number of bent portions 360 possible is included in the antenna element 340, as there appears to be a direct relationship between the beneficial effect provided by the system 320 including the antenna element 340 and the number of bent portions 360 in the antenna element 340.

The system of the invention has been found to provide beneficial effects. For example, a subject suffering from fibromyalgia, osteoarthritis, emphysema and thyroid syndrome used the system 220 in the subject's residence for approximately 11 months. By the end of that period, without using immune system stimulators or other similar medications, the fibromyalgia and the thyroid syndrome appeared to be healed, and the osteoarthritis and emphysema symptoms were considerably alleviated. Fibromyalgia is generally understood to be incurable, and treatments for this disease are typically directed to alleviating symptoms and pain control. In view of this, the apparent effect of the system 220 on the subject is somewhat surprising. Test results indicate that the subject's immune system is now functioning normally.

Another subject was suffering from thyroid syndrome. The subject used the system 220 in the subject's residence for approximately 7 months. By the end of that period, the subject was no longer suffering from thyroid syndrome. The improvement in the subject's condition appears to be attributable to the subject's use of the system 220.

In yet another example, a subject suffering from diabetes routinely had blood sugar readings of 15 and higher. After using the system 220 for approximately three months, the subject's blood sugar readings were much decreased, with an average over 14 days of about 10 or below. The subject's condition appears to be improving, apparently because of use of the system 220. The only significant change in the subject's environment during the relevant time period appears to have been the introduction of the system 220.

In each of the foregoing three examples, the system of the invention appears to have caused a marked improvement in an ill person's condition. In each example, the effect of the system is a surprising result.

One plausible theory is that, when the system 220 removes streams of distorted high-frequency electromagnetic radiation, a subject's immune system is relieved of the stress imposed on it by the streams. When the subject's immune system is thus relieved, the immune system recovers gradually over several months, eventually becoming fully operational. As the immune system recovers, it also is able to resist, with improved effectiveness, the other foreign bodies or agents (e.g., the foreign bodies which may cause fibromyalgia). Ultimately, once the immune system is functioning normally, the immune system succeeds in resisting the diseases in question. However, it will be understood that the foregoing is only a plausible description of the mechanism(s) which may be operative. In any event, regardless of the mechanistic explanation, the system 220 has had a beneficial effect on a number of subjects.

Figure 7:
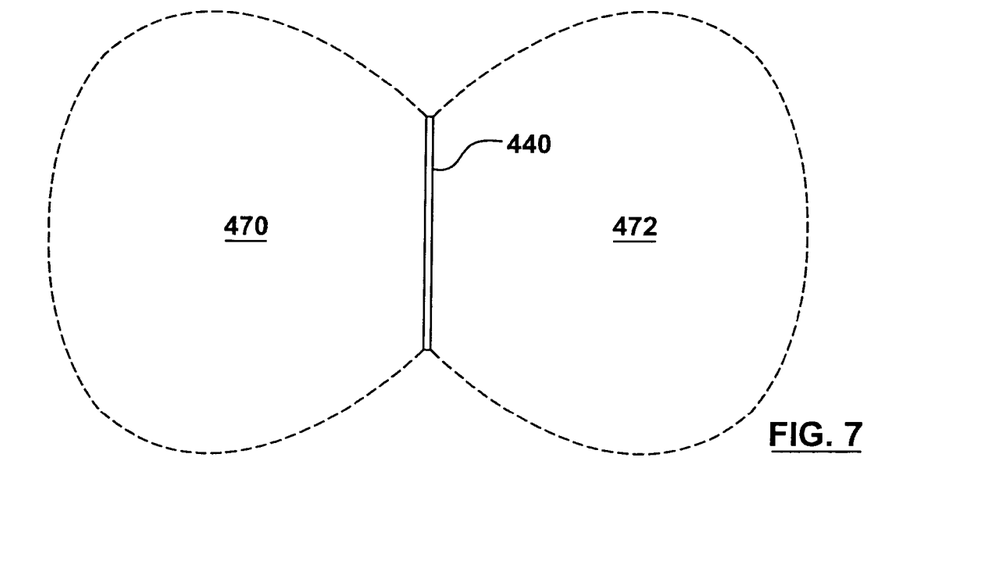
FIG. 7 is a plan view of an alternative embodiment in which the antenna is a dipole antenna, showing the areas covered thereby, drawn at a smaller scale.
Figure 8:
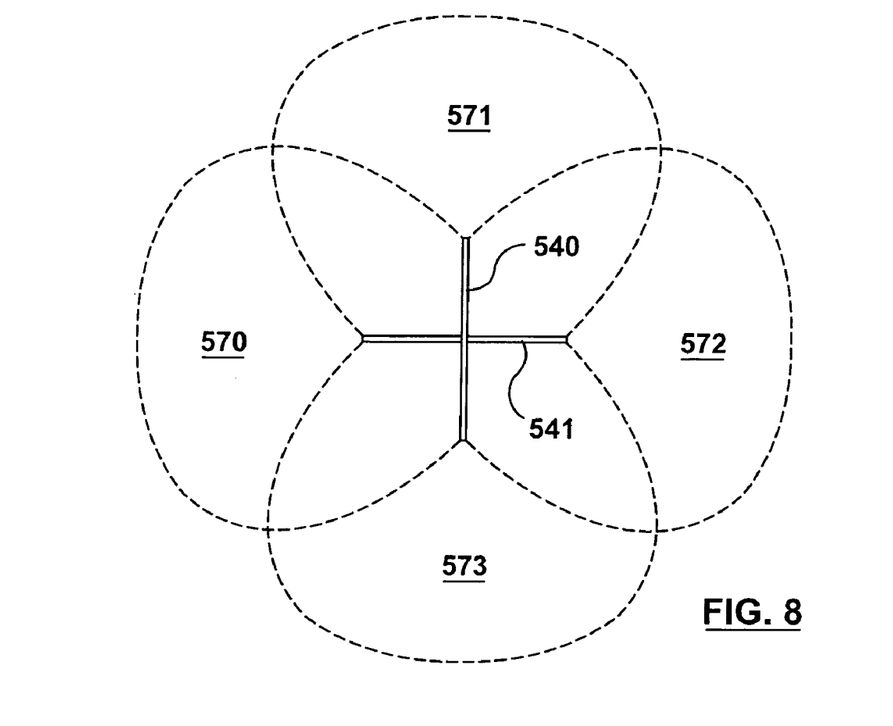
FIG. 8 is a plan view of another alternative embodiment in which an antenna assembly includes two dipole antennas positioned substantially orthogonally to each other, showing the areas covered thereby.

As shown in FIG. 7, a dipole antenna 440 provides coverage over a first area 470 and a second area 472, the areas 470, 472 being positioned on opposite sides of the antenna 440. Depending on the shape of the area for which protection against the streams of distorted high-frequency electromagnetic radiation is sought, one or more antennas may be used together to provide coverage over areas approximately having the desired shape and size. For example, in FIG. 8, a first dipole antenna element 540 and a second dipole antenna element 541 are positioned at right angles to each other, providing respective areas of coverage 570 and 572, and 571 and 573, as shown.

Figure 9:
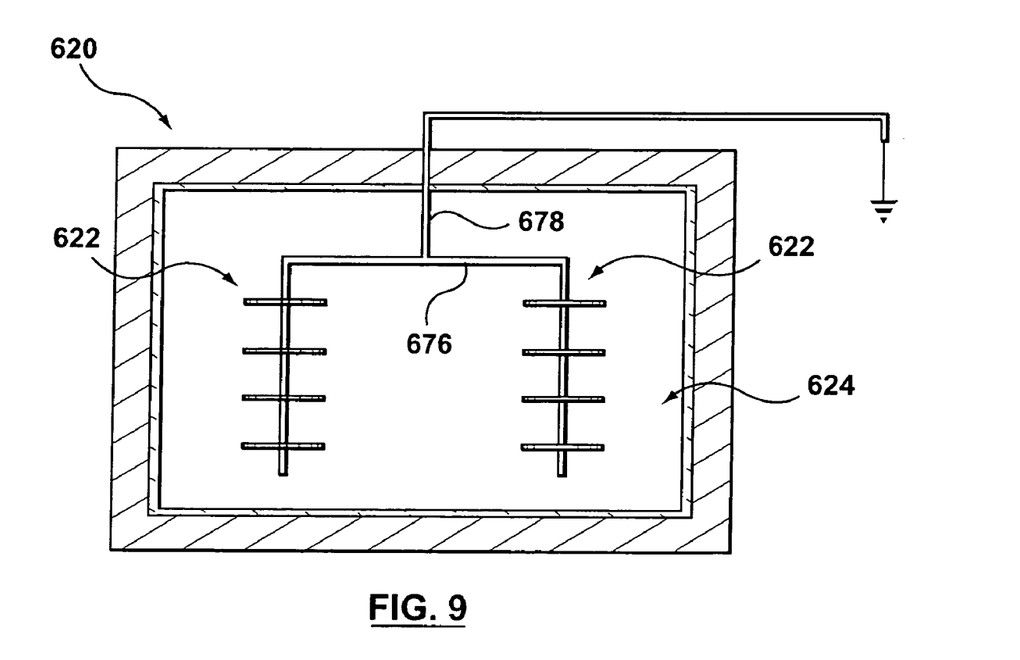
FIG. 9 is a cross-section of another alternative embodiment of the system of the invention, drawn at a larger scale.
Figure 10:
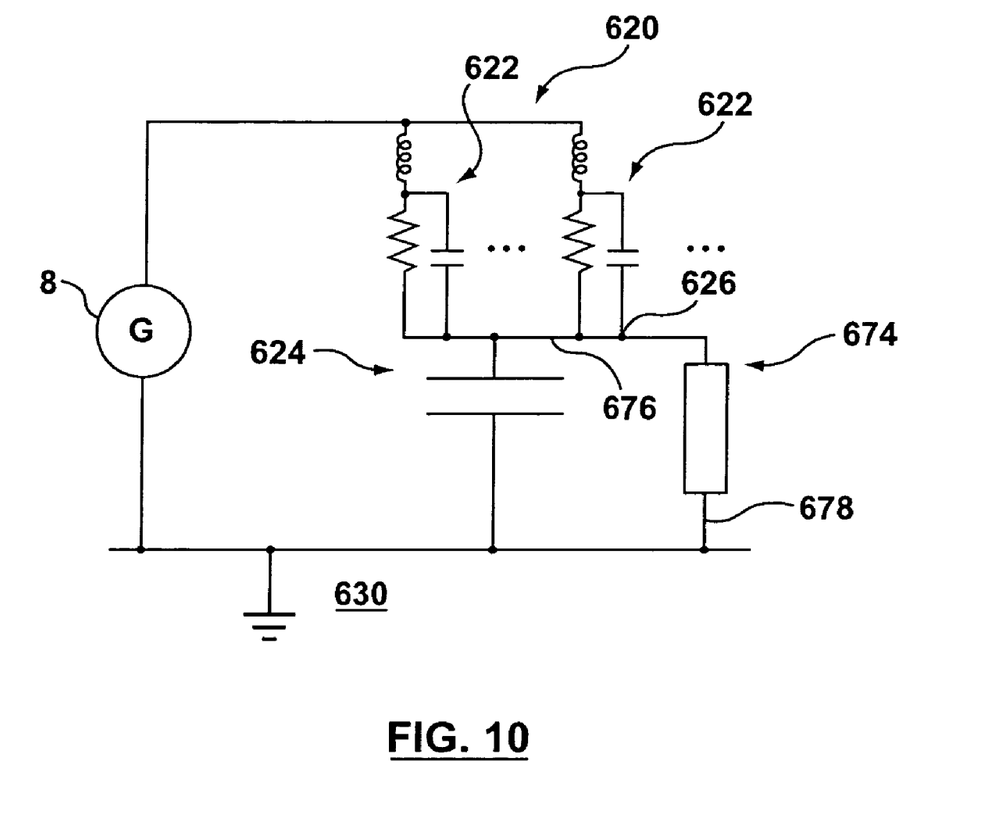
FIG. 10 is a schematic (circuit) diagram of the system of FIG. 9.

In FIG. 9, a cross-section of a system 620 is shown. A schematic (circuit) diagram of the system 620 is also shown in FIG. 10. The system 620 includes at least two antennas 622 for receiving the distorted electromagnetic radiation and at least one capacitor 624 which is electrically connected to the antennas 622. The capacitor 624 has a first electrical potential at a terminal 626. The system 620 additionally includes a conductor assembly 674 for conducting a current flow from the capacitor 624 to a grounding body 630. The grounding body 630 has a second electrical potential lower than the first electrical potential.

The conductor assembly 674 includes a first conductor portion 676 electrically connecting the antenna 622 and the terminal 626 to each other. The conductor assembly 674 also includes a second conductor portion 678 electrically connected to the terminal 626 for conducting a current flow from the capacitor 624 to the grounding body 630. The use of the two antennas 622 has been found to double the range of the coverage provided by the system 620, i.e., as compared to using one of the antennas alone as shown in FIGS. 2B, 2C.

It will be appreciated by those skilled in the art that the invention can take many forms, and that such forms are within the scope of the invention as claimed. Therefore, the spirit and scope of the appended claims should not be limited to the descriptions of the preferred versions contained herein.

I claim:

1. A system for removing at least one stream of distorted high-frequency electromagnetic radiation, said at least one stream being directed substantially in a first direction from the Earth's surface and creating a distorted electromagnetic field, the system having:
    an antenna for receiving the electromagnetic radiation;
    a capacitor electrically connected to the antenna for converting the electromagnetic radiation into a form of potential energy with a frequency equivalent to zero and for storing said potential energy;
    the antenna and the capacitor comprising an interior assembly, the interior assembly including at least one antenna element and at least one support structure to position said at least one antenna element such that said at least one antenna element is aligned substantially in a second direction which is substantially orthogonal to the first direction,
whereby said at least one stream is substantially removed upon the conversion of the electromagnetic radiation into said potential energy.

2. A system according to claim 1 in which said at least one antenna element comprises a disk of relatively electrically conductive material having a predetermined thickness measured substantially in the first direction and a predetermined radius measured substantially in the second direction to an outer edge with at least one notch therein, said notch comprising an opening extending inwardly from the outer edge through the disk substantially parallel to the first direction.

3. A system according to claim 2 in which said at least one antenna element includes a top surface which is substantially planar and a substantially planar bottom surface disposed substantially parallel to the top surface, said surfaces being positioned substantially orthogonal to the first direction.

4. A system according to claim 2 in which said at least one antenna element includes at least one bent portion disposed adjacent to said at least one notch and a remainder portion positioned adjacent to said at least one bent portion, said at least one bent portion having a top surface and a substantially opposed bottom surface, each of said top and bottom surfaces being non-coplanar with a top surface and a bottom surface of the remainder portion respectively, each of the top and bottom surfaces of the remainder portion being substantially planar and substantially parallel to each other, said top and bottom surfaces of the remainder portion being positioned substantially orthogonally to the first direction.

5. A system according to claim 1 in which the interior assembly comprises a plurality of antenna elements.

6. A system according to claim 1 in which said at least one antenna element has a preselected shape selected to provide coverage with respect to said streams of distorted high-frequency electromagnetic radiation over a predetermined geographic area.

7. A system according to claim 6 including two or more antenna elements, each said antenna element having a preselected shape selected to provide coverage over two or more corresponding predetermined areas.

8. A system according to claim 2 in which the predetermined thickness of said at least one antenna element is selected to provide coverage over a preselected distance from the said at least one antenna element.

9. A system for removing at least one stream of distorted high-frequency electromagnetic radiation, said at least one stream being directed substantially in a first direction from the Earth's surface and creating a distorted electromagnetic field, the system having:
   at least two antennas for receiving the electromagnetic radiation;
   at least one capacitor electrically connected to said at least two antennas for converting the electromagnetic radiation into a form of potential energy with a frequency equivalent to zero, and for storing said potential energy to create a first electrical potential at a terminal of said at least one capacitor;
   a conductor assembly for conducting a current flow from said at least one capacitor to a grounding body, the grounding body having a second electrical potential lower than the first electrical potential to create a difference of potentials, the conductor assembly including:
      a first conductor portion electrically connecting said at least two antennas and the terminal on said at least one capacitor;
      a second conductor portion electrically connected to the terminal for conducting the current flow from said at least one capacitor to the grounding body;
      the current flow being caused by the differences of potentials,
   said at least two antennas and said at least one capacitor comprising an interior assembly; and
   the interior assembly including at least two antenna elements and at least one support structure to position each said antenna element such that each said antenna element is aligned substantially in a second direction, the second direction being substantially orthogonal to the first direction,
   whereby said at least one stream is substantially removed upon the conversion of the electromagnetic radiation into said potential energy.

10. A system according to claim 9 in which each said antenna element comprises a disk of relatively electrically conductive material having a predetermined thickness measured substantially in the first direction and a predetermined radius measured substantially in the second direction to an outer edge with at least one notch therein, said notch comprising an opening extending inwardly from the outer edge through the disk substantially parallel to the first direction.

11. A system according to claim 10 in which each said antenna element includes a top surface which is substantially planar and a substantially planar bottom surface disposed substantially parallel to the top surface, said surfaces being positioned substantially orthogonal to the first direction.

12. A system according to claim 10 in which each said antenna element includes at least one bent portion disposed adjacent to said at least one notch and a remainder portion positioned adjacent to said at least one bent portion, said at least one bent portion having a top surface and a substantially opposed bottom surface, each of said top and bottom surfaces being non-coplanar with a top surface and a bottom surface of the remainder portion respectively, each of the top and bottom surfaces of the remainder portion being substantially planar and substantially parallel to each other, said top and bottom surfaces of the remainder portion being positioned substantially orthogonal to the first direction.

13. A system according to claim 9 in which the interior assembly comprises a plurality of antenna elements.

14. A system according to claim 9 in which each said antenna element has a preselected shape selected to provide coverage with respect to said streams of high-frequency electromagnetic waves over a predetermined geographic area.

* * * * *